(12) United States Patent
Alford

(10) Patent No.: US 12,708,556 B2
(45) Date of Patent: Aug. 18, 2026

(54) HYPERTHERMIA TREATMENTS, DEVICES, PROCESSES, AND SYSTEMS

(71) Applicant: Starfish Neuroscience Inc., Bellevue, WA (US)

(72) Inventor: Jamu K. Alford, Port Orchard, WA (US)

(73) Assignee: Starfish Neuroscience Inc., Bellevue, WA (US)

( * ) Notice: Subject to any disclaimer, the term of this patent is extended or adjusted under 35 U.S.C. 154(b) by 0 days.

(21) Appl. No.: 19/288,807

(22) Filed: Aug. 1, 2025

(65) Prior Publication Data

US 2026/0033982 A1 Feb. 5, 2026

Related U.S. Application Data

(60) Provisional application No. 63/679,392, filed on Aug. 5, 2024.

(51) Int. Cl.
*A61F 7/00* (2006.01)

(52) U.S. Cl.
CPC ...... *A61F 7/007* (2013.01); *A61F 2007/0077* (2013.01); *A61F 2007/0095* (2013.01)

(58) Field of Classification Search
CPC ................................ A61F 7/007; A61N 1/403
See application file for complete search history.

(56) References Cited

U.S. PATENT DOCUMENTS 7,729,778 B2 6/2010 Eggers et al.
9,295,517 B2 3/2016 Peyman et al.
12,239,855 B2 3/2025 Tabatabaei
2009/0082832 A1 3/2009 Carbunaru et al.
2016/0067497 A1* 3/2016 Levine ................. A61B 5/4047 607/62
2017/0054319 A1 2/2017 Kesler et al.
2022/0168579 A1 6/2022 Robinson et al.
(Continued)

FOREIGN PATENT DOCUMENTS

CN 111759460 10/2020
JP 2005253813 9/2005
(Continued)

OTHER PUBLICATIONS

International Search Report and Written Opinion for International PCT Patent Application No. PCT/US25/40376 mailed Oct. 27, 2025 (14 pages).

*Primary Examiner* — Kaitlyn E Smith
(74) *Attorney, Agent, or Firm* — Foster Garvey PC

(57) ABSTRACT

In accordance with principles of the invention, one or more embodiments are provided of an implant that in use is embedded in a body and generates heat treatment that treats cells in a surrounding area. The device may be wireless and be configured to operate using energy harvesting of RF waves from an external coil and system. The device can be part of such systems and can involve multiple devices for providing simultaneous treatment. The device can be configured to operate to transition between two operating modes when receiving the RF waves that switch the power level of the operating circuit to autonomously move from a low power level that powers a microcontroller and a high power level that powers the microcontroller and generates heat that applies desired treatment to target tissue.

21 Claims, 6 Drawing Sheets

(56) References Cited

U.S. PATENT DOCUMENTS

| | | | | |
|---|---|---|---|---|
| 2022/0273359 | A1 | 9/2022 | Cohen | |
| 2022/0313476 | A1 | 10/2022 | Harmer et al. | |
| 2023/0405340 | A1 * | 12/2023 | Robinson | A61N 1/0534 |
| 2025/0152235 | A1 | 5/2025 | Gambhir et al. | |

FOREIGN PATENT DOCUMENTS

| | | |
|---|---|---|
| JP | 2007190083 | 8/2007 |
| JP | 2011251042 | 12/2011 |
| JP | 2019193748 | 11/2019 |

* cited by examiner

HYPERTHERMIA TREATMENTS, DEVICES, PROCESSES, AND SYSTEMS

CROSS REFERENCE TO RELATED APPLICATIONS

This application claims the benefit of priority to U.S. Provisional Patent Application No. 63/679,392, filed on Aug. 5, 2024. The entire contents of this patent application are herein incorporated by reference.

The present invention relates to hyperthermia treatments including devices, processes, medical treatments, or systems.

BACKGROUND

In known systems, highly localized hyperthermia can be achieved inside the body by using focused ultrasound, and on the surface of the body by using heating pads with infrared lights. However, existing therapies are either expensive or don't target deeper structures. In the case of focused ultrasound heating, the therapy requires complex phased-array ultrasound transmitters that must be used in conjunction with magnetic resonance imaging (MRI) thermometry. While these systems exist, they are rare and cost many millions of dollars and are not scalable to the treatment of large number of people. In the case of surface heating devices, high anatomical specificity can be achieved on the skin but not significantly below the surface. Attempting to use surface methods to reach deeper targets results in significant off-target effects and possible overheating (burning) of the surface tissue.

These and other deficiencies or drawbacks in the prior art sought to be addressed by one or more embodiments of the present.

SUMMARY

In accordance with principles of the invention, one or more embodiments are provided of an implant that in use is embedded in a body and generates heat treatment that treats cells in a surrounding area. The device may be wireless and be configured to operate using energy harvesting of RF waves from an external coil and system. The device can be part of such systems and can involve multiple devices for providing simultaneous treatment. The device can be configured to operate to transition between two operating modes when receiving the RF waves that switch the power level of the operating circuit to autonomously move from a low power level that powers a microcontroller and a high power level that powers the microcontroller and generates heat that applies desired treatment to target tissue.

For example, a medical treatment implant for treating cancer for an extended period in a patient's body can be provided, which comprises, an electrical circuit comprising, a microcontroller that is configured to store a temperature, a first inductor, a first capacitor, a ferromagnetic core that is adapted to interact with the inductor to generate heat to treat a target area of a body, wherein the first inductor and first capacitor configure a resonant frequency of the electrical circuit, and are adapted to receive wireless electromagnetic waves and in response, produce power at a first level that is capable of powering operation of the microcontroller and the ferromagnetic core to treat a target area of the body.

The implant further comprising a semiconductor switch that is adapted to reduce power to a second level below the first level, by selectively activating a second inductor, a second capacitor, or an additional circuit component, wherein the second level is capable of powering operation of the microcontroller.

In some embodiments, the electrical circuit may include a second inductor adapted to be associated with the ferromagnetic core and when activated, produces a magnetic field that modifies a magnetic field associated with the first inductor.

In some embodiments, the semiconductor switch comprises two or more metal oxide semiconductor field effect transistors (MOSFETs).

In some embodiments, the electrical circuit includes a rectifier and a regulator that are adapted to produce a DC voltage that powers the microcontroller.

In some embodiments, the electrical circuit, using the first inductor and first capacitor, is configured to receive amplitude modulated RF waves that carry digital information.

In some embodiments, the electrical circuit is adapted to transmit information using backscatter communications.

In some embodiments, the electrical circuit is adapted to selectively vary power consumption among two or more levels that communicates digital information to an external device that is monitoring the medical implant.

In some embodiments, the electrical circuit is configured to store an identifier and vary power use of the electrical circuit to communicate the identifier to an external device.

In some embodiments, the semiconductor switch selectively inserts a Zener diode into operation.

In some embodiments, the electrical circuit is configured to automatically and independently active or deactivate the semiconductor switch based on the local temperature.

In some embodiments, the electrical circuit is configured to generate heat using the ferromagnetic core that changes the tumor microenvironment.

In some embodiments, the microcontroller comprises a temperature sensor.

In some embodiments, a temperature sensor is included that is configured to communicate with the microcontroller.

In some embodiments, the electrical circuit is configured to transmit a local temperature.

In some embodiments, a system may be provided comprising, a plurality of heat generating wireless implants, wherein each implant comprises a ferromagnetic core that generates heat to treat adjacent cancer cells in a body, a semiconductor switch that automatically and independently activates the ferromagnetic core based on temperature sensed at or about the implant, and an inductor and capacitor combination that converts RF waves to energy that operates the implant, and a microcontroller that varies current load in the implant to wireless transmit an implant identifier and sensed temperature; and an apparatus positioned external to the body that generates RF waves to provide wireless power to the implants and receives identifiers and sensed temperatures from individual implants.

In some embodiments, the apparatus is configured to transmit an RF wave at a certain frequency whereby the implants are configured to generate heat selectively at different locations based on the implant's sensed temperature.

In some embodiments, each implant is configured to transmit the identifier using backscatter communications.

In some embodiments, each implant is configured to operate to stay within a sensed temperature of 37° C. to 60° C.

In some embodiments, the semiconductor switch modifies inductance, capacitance, or loading characteristic of an electrical circuit operating in the implant to activate or deactivate heating by the ferrite core that treats a targeted area of the body.

In some embodiments, the semiconductor switch is a single MOSFET.

In some embodiments, the implant receives and stores a maximum temperature transmitted from the external device.

In some embodiments, the implant limits heating once the measured temperature surpasses the stored maximum temperature.

In some embodiments, a device is provided that is implanted in a human body, the device comprising a an inductive coil and support such a ferromagnetic core, wherein the device can be positioned by implant to treat a target internal to the body and wherein the wireless power is applied to the device to generate heat that is applied to the target.

In some embodiments, a body implant is provided to be implanted for an extended period comprising wireless power, without a battery, and a semiconductor switch that varies between two levels of power generated by the implant.

In some embodiments, a body implant is provided that is configured to independently control intermittent tumor heat therapy while maintaining power to a microcontroller when designated heat therapy is turned off.

In some embodiments, a system is provided that comprises multiple body heat-treatment implants that independently operate and send unique digital identifiers to an external system.

In some embodiments, a system is provided that comprises multiple body implants that are each powered by RF electromagnetic waves at a frequency and operate by using the RF electromagnetic waves to heat target tissue at a temperature of about 38 to 43° C., the implant comprising an operating mode that rejects some of the energy in the RF electromagnetic waves as part of maintaining the temperature in the range.

The embodiments illustratively described herein primarily describe an implant or implant system that has two levels of power and selectively switch between the two power levels. This is not to say that all embodiments are limited to two levels and such switching. In some embodiments, the implant or implant system is configured to strictly have the two switchable power levels for controlling the heating during the heat treatment and in some embodiments, the implant (and therefore the implant electrical circuit) has three or more power levels or power modes.

BRIEF DESCRIPTION OF THE DRAWINGS

The accompanying drawings, which are incorporated herein and constitute part of this specification, are illustrative of particular embodiments of the present disclosure and do not limit the scope of the present disclosure. The drawings are not to scale and are intended for use in conjunction with the explanations in the following detailed description.

DESCRIPTION OF EMBODIMENTS OF INVENTION

Figure 1:
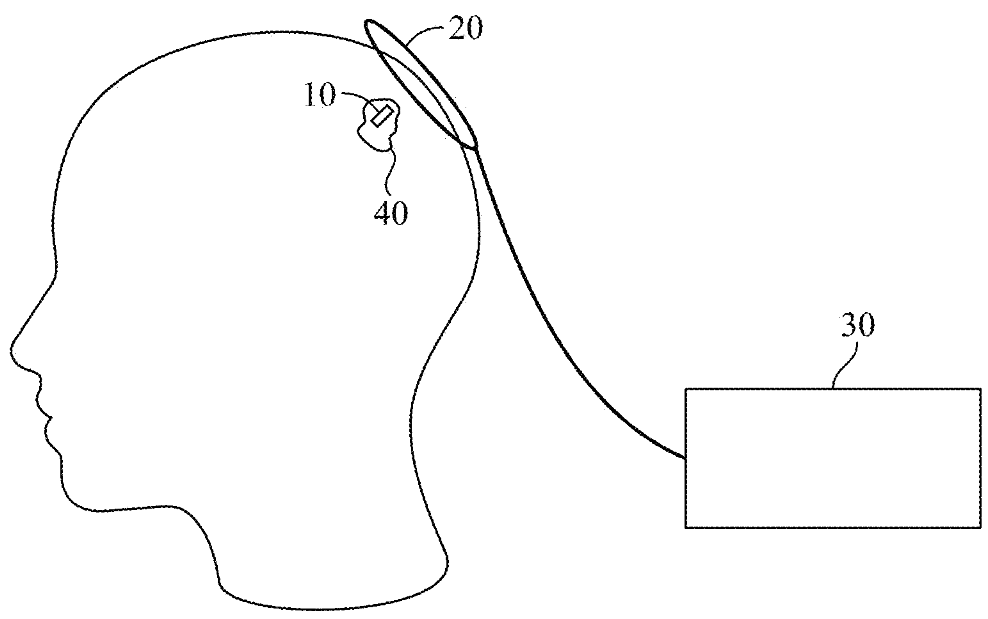
FIG. 1 is a diagram of an exemplary hyperthermia treatment apparatus, in accordance with one or more embodiments of the present invention(s).

Embodiments of the present invention involve a system to provide medical therapy, initially developed for oncology, but which may also be useful in treating other conditions.

Regional increases in body temperature for clinical use, called hyperthermia therapy, can be used to modify the cellular behavior of body tissue by up or down regulation of specific cellular functions, as well as destroy tissue by denaturing proteins and killing cells.

Apparatus and method described herein are directed to a plurality of objectives and embodiments. A first objective is to provide an implant that has a size or footprint that is suitable for being implanted inside a body (in vivo) at a location in or adjacent to tissue that is the target of the treatment. The implant is desired to be implanted in the body for an extended period of time to allow the patient to receive repeated treatments over time. The size of the implant is sought to be small such that it is easily injected into the body without interfering with body operations in the areas used for the implant.

A related objective is to be functionally operable using battery-free wireless power. A battery can have a significant impact on the size and length of operation of the implant. Also, a battery may have harmful chemicals which may pose a risk to the patient. A "tether" or electrical wire connecting the implant to an external power supply raises risks such as infections and complexity of routing the wire through the body without causing harmful consequences to the patient.

Another objective is to be able to treat multiple body regions at the same time. For example, cancer cells may be positioned in (spread to) different areas of the body. Each region may have different characteristics such as size or type. An objective would be to variably treat each region with hyperthermia. The implants would be able to selectively activate to match the local characteristics of that implant.

Another objective is to confirm that the treatment has been applied. The implants can transmit information about the local temperature to an external system to confirm the treatment. As mentioned, minimizing the size of the implant and having efficient energy consumption are also important. The implant may be configured to modify electromagnetic fields based on its operation to communicate digital information such as temperature to an external system.

An objective of reducing the size of the implant, increasing operable life, and reliability can be contributed to by reducing or eliminating on-board components or features such as by configuring the implant to control operation autonomously subject to receiving wireless energy.

In the context of an implant that is left in the body for a long duration, minimization of size, energy usage, and complexity are important objectives that can lead to advantages of minimal physical risk from implantation and reduced likelihood of needing to be replaced during the treatment period. Further, in the context of implants that are in vivo for an extended period, receiving confirmation of operation is an important objective. A feature that provides this with reduced complexity or addition to the structure of the implant can enhance the performance of the implant.

A high Q (or quality) factor material such as a ferromagnetic core can be used in combination with an inductance and capacitance arrangement to generate heat using the ferromagnetic core, such as, a ferrite core, when the circuit receives wireless electromagnetic waves at a resonant frequency of the inductance and capacitance arrangement for receiving electrical waves. Most heating occurs in the ferrite core, but additional heating can also occur the coil and capacitive elements that make up the circuit. A microcontroller can be configured to be supplied power from the inductance and capacitance arrangement. The microcontroller may include a temperature sensor or may receive temperature information for its environment from another device such as temperature sensor. Preferably, heat generated by the high Q factor material is controlled to be at or below a level that destroys or damages tissue but is at a level, for example, that weakens or sensitizes cancer cells. Other forms of treatments such as cancer treatments can be applied to the body in conjunction with the hyperthermia treatment to treat the weakened/sensitized cells. Information about the threshold (maximum) local temperature or therapeutic temperature range can be stored on the implant such as on the microcontroller and can be used by the microcontroller to selectively turn on or off heat treatment generated by the high Q factor material.

A high Q factor material, as used herein, means that the ratio of electrical energy stored to energy dissipated (heat) for each oscillation of the inductor is greater or equal to 10. A ferromagnetic core may particularly suitable for this application because of its structural and mechanical properties.

It should be understood that the heating aspect of the implant is an analog electrical arrangement, and such operation is not necessarily an immediate transition in state but can involve a transition period for example as energy dissipates in the core. Also, as discussed herein, in the off state there will be some energy at a lower level harvested from the electromagnetic waves to supply the operation of the microcontroller. This energy generation will interact with the core but at a lower level such that it is configured not to activate heat treatment for the target area.

The microcontroller can control the treatment to stop generating heat until a lower local temperature is reached and in response, it can activate heat generation again. To turn off heat generation the microcontroller is arranged with other switch controlled circuitry that reduces the energy captured by the inductance-capacitance arrangement to a desired level using a selective modification to the inductance, capacitance, or resistive loading in relation to the inductive-capacitance arrangement that harvests energy from transmitted electromagnetic waves at a particular frequency that is constantly being transmitted to the implant.

A semiconductor switch can be implemented to apply the selective modification. The selective modification can reconfigure the implant to be in a second operational mode in which power is supplied from the inductance-capacitance arrangement at a lower level that turns off heating (understood to exclude some inherent minor heating, for example, because of continued inductance-capacitance energy generation) but is capable to power the operation of the microcontroller and other components operating during this standby or low power mode and be able to operate the microcontroller to activate the “on” mode.

The implant circuitry can be configured to receive information using the electromagnetic waves generated to power the inductance-capacitance energy generation. Amplitude modulation can be implemented in the electromagnetic waves to carry information to the implant. The implant can include a demodulation process involving a rectifier, regulator, and the microcontroller to identify digital data bits in the transmitted waves. The implant can use backscatter technology to transmit implant identifier, temperature, or other information to the external system. The implant can selectively vary the operation of electronics, onboard/carried by the implant, which in response changes the electromagnetic field. An external system can monitor the electromagnetic field and demodulate information from the implant-initiated variations in the field.

Embodiments of the present invention provide for an electrical circuit that avoids (substantially avoids) in operation the use of mechanical components. For example, preferably, the switch is a semiconductor switch that controls the flow of electrons without a mechanical operation to change the path. As used herein, a semiconductor switch means a switch made using a semiconductor fabrication process and without incorporating a mechanical arm or bar in the structure.

Embodiments of the present can meet one or more of the objective by providing an electrical circuit for a body implant that is configured for extended use where the electrical circuit comprises, consists of, or consists essentially of a capacitor and an inductor, wherein the combination of capacitance and inductance is configured to generate energy (electrical current) from received RF waves transmitted at a resonant frequency of the inductance-capacitance combination, a ferromagnetic core that has the inductor wrapped around the core to generate heat that treats surrounding body tissue at first heating or energy level, a temperature sensor, a microcontroller, and a semiconductor switch that is controlled by the microcontroller based on vicinity temperature information from the temperature sensor and when activated by the microcontroller adds into or removes from operation one or more circuit components that electrically or magnetically interact with the operation of the energy generation to reduce heat/energy generated by the ferromagnetic core to a lower level that permits the temperature to dissipate to or below a threshold level. In operation, the electrical circuit can be configured to turn off heat treatment (move to a lower level) when the measured temperature is above a threshold. The electrical circuit can be configured to transmit temperature information to an external system, but the electrical circuit is preferably configured to be under independent control from the external system (except for possibly receiving energy and temperature threshold setting(s)). The electrical circuit may include other electrical components that do not substantially contribute to the one or more objectives.

In general, it would be understood that “electrical circuit” refers to a combination of electrical components that are carried by the implant that operate to provide the desired heat treatment.

FIG. 1 is a diagram that illustrates a treatment system in accordance with one or more embodiments of the presentation invention. The system is labeled 10, 20, 30 and the tissue to be treated is labeled 40. The system comprises implantable device 10, an external radiofrequency coil 20 used for transmitting power and receiving data, and control electronics 30 which includes a radiofrequency transmitter/receiver pair and computer.

As shown in FIG. 1, the system can include a tiny, active (meaning it has onboard digital logic electronics) medical device that can be injected or inserted into the human body at specific locations (and depths) to create a local increase in temperature. The system can include a second device that is external to the human body, which provides wireless energy and communication. A control system is included that specifies the maximum temperature of the injected device(s), which provides wireless power and verifies the actual device temperature.

The injectable device has, for example, four features. First, it collects radiofrequency (RF) energy from the external device and converts it to heat. Once the injectable device reaches a maximum or desired treatment temperature, a setpoint, as specified by the clinician via the control system and stored on the implantable device, the device will cease or significantly reduce treatment level heat generation until sensed temperature falls below the threshold. The system can turn the heat on and off to maintain a setpoint temperature. If desired, a wireless readout indicating the current temperature of the injectable device can be included. It can provide important information on the state of the device, especially if it is failing to reach the setpoint temperature, such as due to incorrect placement of the external device, i.e., it is not receiving sufficient power. The system 30 would use this information to indicate to the operator that either the power should be increased and/or the external device positioned nearer to the implant. This feature could also be used to control the temperature of a single implant without an internal setpoint. The implant may be used singularly or in multiples around the target tissue. Multiple implants may result in more uniform heating or heating of a larger volume of tissue. Given that each implant may be positioned at a different distance from the external device, coil 20, and therefore receive a different amount of wireless energy, it is preferably configured to have each implant independently control its heating operation when its individual threshold temperature is achieved.

The implant device 10 is placed in the body to create a localized, controlled heating of tissue. As noted, multiple implants may be used to treat different regions in the body (e.g., simultaneously).

The external antenna 20, sometimes called a coil or transmit coil, sends radiofrequency (RF) energy to the device 10. It can also send and receive RF signals to the device 10 to set the temperature and receive temperate data from the implant. The RF signals can be carried by radiofrequency energy. The carrier frequency of the radiofrequency energy is chosen to limit absorption in the tissue, generally called specific absorption of radiation (SAR). The frequency may also be chosen to fall within Federal Communication Commission (FCC) regulations or similar regulations. Typically, this is in the range of 100 kHz to 400 kHz but could be within a wider range of 30 kHz to 14 MHz provided that the system satisfies FCC rules.

The system controller 30 includes a radiofrequency transmitter/receiver that provides power and digital information to antenna or coil 20 and receives data from antenna or coil 20. It can also interface with clinical operators via a screen and input device, such as a keyboard, but may also have remote communication via wired connections or wireless connections including Bluetooth and Wi-Fi. It may also send or receive information from a remote Internet site. System controller 30 can be for example a computer that includes software on non-transitory computer readable medium that stores computer readable instructions that when executed by the computer performs operations as described herein. The instructions configure the controller operation and interaction for the treatment. In some instances, the external device may have two coils, one for Transmit and a Second to receive the backscattered information. In other instances, a single coil would provide both functions.

For small targets (tissue to be treated 40), as shown in FIG. 1, a single implant may be ideal; for larger target regions several implants may be used to treat the entire volume. The device may be injected or surgically implanted or placed within a blood vessel like a stent to treat a nerve that wraps around the vessel such as the renal nerve for hypertension.

Figure 2:
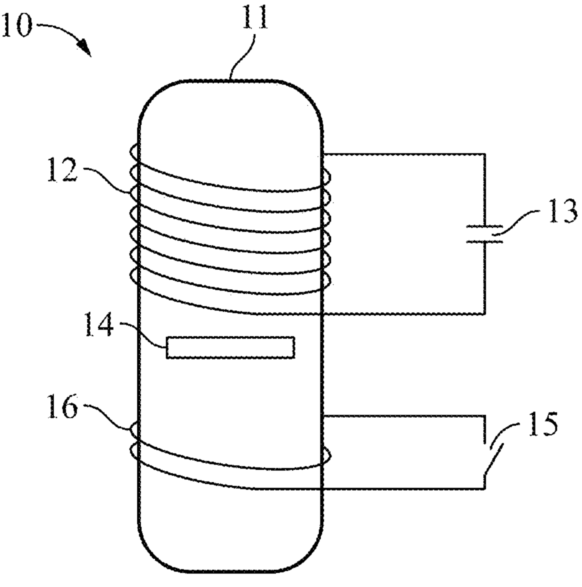
FIG. 2 is a diagram of an exemplary implant, in accordance with one or more embodiments of the present invention(s).

FIG. 2 provides a diagram illustrating an example embodiment of the device 10 in accordance with an embodiment of the present invention. The implantable (e.g., injectable) device 10 has the following subcomponents: a ferromagnetic core 11, an inductor (coil) 12, which with, a capacitor 13, makes an inductive-capacitive (LC) resonant circuit (arrangement). A microchip 14 which can measure the local device temperature, report the temperature by high-speed modulation of the switch 15 (preferably a semiconductor switch) and control heating by closing the switch. A secondary coil 16, called the choke coil can be used to limit input power to the inductive-capacitive arrangement and send information back to the external transmit coil.

A ferromagnetic core 11 is an important component as it allows a significant amount of radiofrequency energy to be collected. The primary coil 12 and secondary coil 16 are wrapped around the ferromagnetic core 11 to electromagnetically interact with the ferromagnetic core 11 in operation.

The primary coil 12 when used with capacitor 13, the values of which are chosen to achieve resonance at the radiofrequency of the external transmitter 20 to optimize the energy harvesting capability of 11.

In this embodiment, the microchip 14 has the following features and capabilities, receives and stores a maximum temperature setpoint via a wireless signal, measure the temperature of the device, and control the state of switch 15 to wirelessly report temperature or stop heating when the maximum temperature is reached. Some implementations or applications may use a subset of these features.

The switch 15 is implemented, in some embodiments, using at least one low on-resistance transistor such as a MOSFET or similar solid state electronic relay. It is preferred for a number of reasons such as size to use a semiconductor switch rather than a switch that includes a mechanical switch or mechanical operation that triggers the switch. The state of the switch is controlled by the microchip 14. During the heating cycle the switch would be in the 'open' condition most of the time and may (only) be closed briefly to send temperature information to computer/system controller 30. During the cooling cycle, when the device has reached its setpoint temperature, the switch 15 would be in the 'closed' condition most of the time, only opening briefly to send temperature information to control computer 30. In this implementation, opening and closing the switch quickly acts to send digital information from the implant to the external device via fluctuations in the radiofrequency magnetic field. This is sometimes called inductive backscattering.

The choke coil 16 typically will have significantly fewer turns of wire compared to the primary coil 12 to reduce the voltage seen by the switch 15. When this switch is quickly opened and closed (meaning switching at a high frequency) it can send digital information back to the external coil 20 and computer 30 using a technique called inductive backscatter. This is because the electrical circuit comprising ferromagnetic core 11, primary coil 12, capacitor 13, choke coil 16, switch 15, and a microchip operate in concert. When the switch 15 is closed the electromagnetic field produced by the circuitry when operating using the RF energy from the external antenna (e.g., antenna 20 in FIG. 1) is varied between two operating states. The produced field is monitored by system 30 to detect information (digital bits) being transmitted by the implant 10.

Together the switch 15 and the choke coil 16 in operation when semiconductor switch 46 is activated can almost completely "block" all radiofrequency energy from entering the ferromagnetic core 11. The switch opens or closes to add or remove choke coil 48 to modify the operation of the electrical circuit 30 between two levels of energy or power supply generated by the resonant inductor-capacitor arrangement (primary coil 12, capacitor 13 and capacitor 15). The frequency of opening and closing the switch 15 at a low rate, low frequency switching, (e.g., on the timescale of seconds), based on measured temperature, controls heating, while frequency of opening and closing it at a high rate (e.g., a timescale of milliseconds) sends data back to the control computer 30 via the coil 20 without changing the heating state when using high frequency signaling. The frequency can for example be at 100 Hz to 100 kHz. At such high frequencies, the switching negligibly affects the state of heating because the heating increases or decreases at a much slower rate compared to the switching for signaling purposes. Thus, the arrangement can provide a dual use of heating and signaling.

If desired, in some embodiments, control of heating can be configured using circuitry in device 10 or another device, combinations thereof.

Device 10 can significantly (meaning more than 90%) reject radiofrequency (RF) energy or reduce the RF energy converted from the RF waves transmitted by the external antenna (e.g., in an off state, even though there may be some residual heating), and therefore limit the maximum temperature once the setpoint has been reached. In this embodiment, this is achieved using the choke coil 16 and switch 15. When the choke coil 16 is activated to enter an off state for the heater, the electromagnetic field generated by the choke coil 16 interacts with the field of the primary coil 12, which consequently modifies the field of coil 12 such that a smaller portion of the energy transmitted in the RF wave is captured by primary coil 12 and capacitor 13. The magnetic field generated by choke coil 16 is arranged to "push" the electromagnetic field out of primary coil 12 (pushed out of optimal position) and consequently, the power produced from wireless-energy conversion in the heating "off" state is moved to be at or above a power level that is sufficient to operably power microchip 14. The power level would be below a power level that is used to generate heat in a treatment state. Therefore, the circuit is preconfigured to have at least two operating modes, one that applies heat treatment to its environment and to power the microcontroller and another that turns off the heat treatment but continues to power the microcontroller. This is performed by the microcontroller to control how much energy is harvested from the transmitted RF wave being transmitted by the external antenna. The RF wave is transmitted at a constant frequency, at the resonant frequency of the electrical circuit, and in this case the resonant frequency established by inductor 12 and capacitor 13. As mentioned, the external system transmits at a constant frequency so that it can support multiple implants in an associated region. Preferably, the transmission is not varied or changed based on the feedback from the implants.

Figure 3:
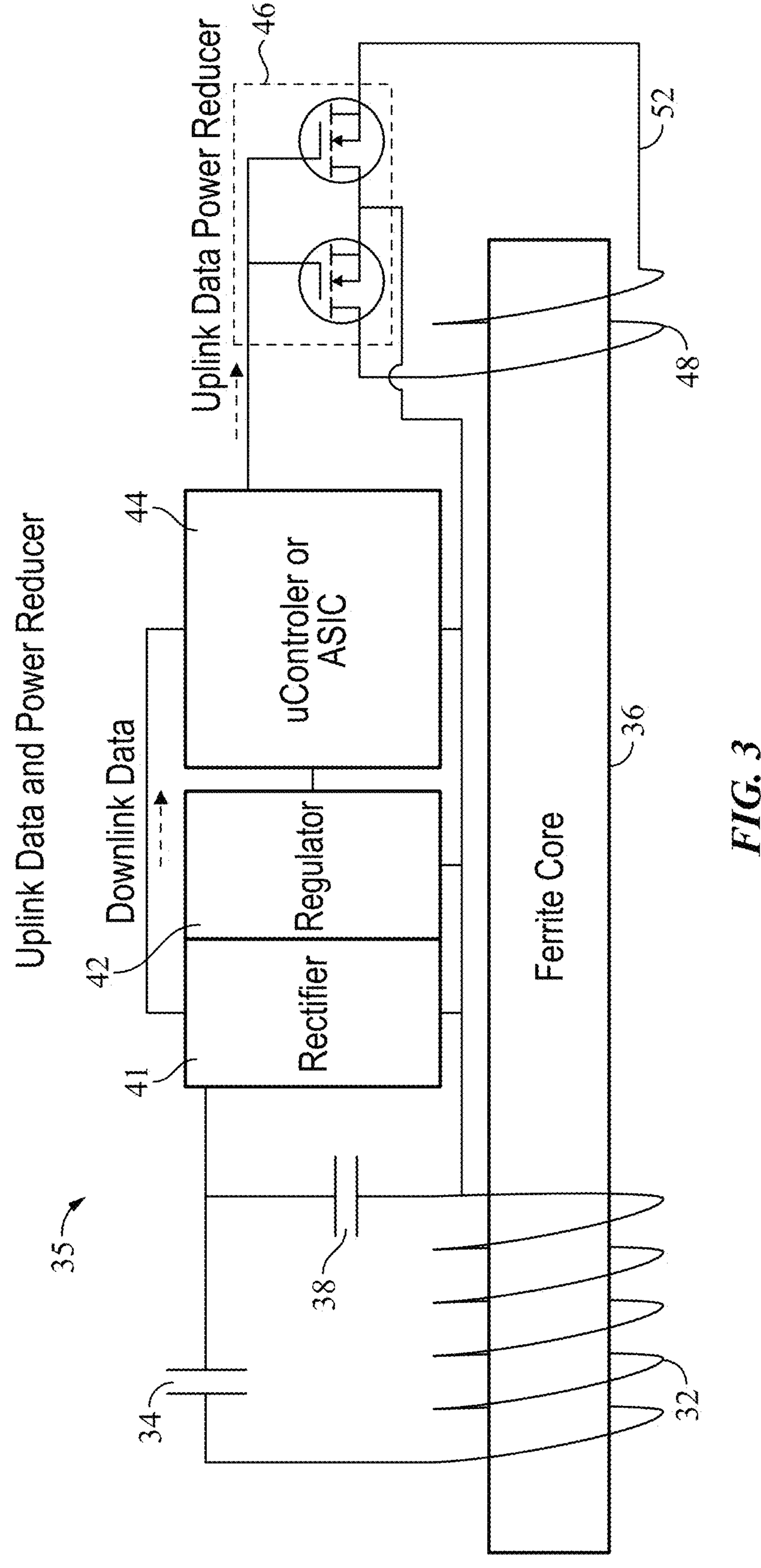
FIG. 3 is a circuit diagram of an exemplary implant, in accordance with one or more embodiments of the present invention(s).

FIG. 3 is an illustrative circuit diagram providing an embodiment based on the electrical circuit of FIG. 2. Electrical circuit 35 comprises primary coil 32, capacitor 34, ferrite core 36, capacitor 38, rectifier 41, regulator 42, microcontroller 44, semiconductor switch 46, and secondary or choke coil 48. Primary coil 32 (which is understood to be an inductor) in combination with capacitors 34 and 48 are selected to establish a desired resonant frequency for the electrical circuit. Equipment external to the body will be configured to transmit RF waves at that resonant frequency. Electric current generated is at a power level that causes the ferrite core 36 to generate heat at a desired level to treat tissue touching or positioned adjacent to (or abutting) the implant (containing the electrical circuit 35). Capacitor 38 can also operate as a voltage divider to prevent damage to the rectifier. The current generated is tapped to flow a portion of the current to the rectifier 41 (which rectifies the AC signal generated by the inductor/capacitor arrangement from the RF waves), which in turn supplies regulator 42. Regulator 42 conditions the electricity to provide a stable DC voltage power supply to the microcontroller 44. Circuity in rectifier 41 or elsewhere can be configured to filter digital signals that were modulated into the transmitted RF waves. Amplitude modulation of the waves can be used to carry digital signals to the electrical circuit 35. The circuitry can rectify and filter signals to generate "1"s and "0"s that were carried in the RF Waves. The signals can carry information such as temperature(s) to be stored in the microcontroller to use as the threshold or otherwise control when heating is turned "on" or "off."

Microcontroller 44 may include a temperature sensor or may receive temperature from another source such as a temperature sensor situated in electrical circuit 35 and physically external to microcontroller 44. The temperature sensor is used to determine a current temperature at or in close vicinity to the implant/electrical circuit. Depending on the configuration, equipment, and location and type of sensor, the microcontroller may have been previously configured to correlate or convert the sensed internal temperature to expected biological temperature external to the implant. Therefore, the sensed temperature may be representative of the current temperature and/or the heating temperature and based on predetermined calculations, it can be used to set the temperature setting for the electrical circuit.

Semiconductor switch 46 comprises two metal oxide semiconductor field effect transistors ("MOSFETs") that are configured to both be open or closed at the same time. Microcontroller 44 is configured to have an output signal that turns the MOSFETs off or on. Since the current through the electrical circuit such as in line 52 can be alternating (e.g., an AC circuit having positive and negative directions), a pair of MOSFETs are implemented and arranged to switch on/off the current in both positive and negative directions.

Secondary coil 48 generates a current from the RF waves transmitted from the external antenna when semiconductor switch 46 is closed. Secondary coil 48 is configured to have an inductance that is compatible with the transmitted RF waves to generate electricity. Secondary coil 48 is also wrapped around ferrite core 36 and the secondary coil 48 and primary coil 32 are magnetically coupled. When semiconductor switch 46 is closed and current is running through secondary coil 48 in response to the transmitted RF waves, the secondary coil 48 generates an electromagnetic field. In FIG. 3, the primary coil 32 and secondary coil 48 appear to the observer to be "far" apart. In implementation, coils 32 and 48 are positioned close to each other. In operation, the electromagnetic field produced by secondary coil 48 will interact with the electromagnetic field of primary coil 32. This interaction causes a modification to the characteristics of the electromagnetic field of the primary coil 32 such as by "pushing" the electromagnetic field of primary coil 32 to a position or configuration that affects (reduces) the current generated. The activation of the secondary coil 48 also changes the resonant frequency to which electrical circuit 35 is tuned. The activation or insertion of secondary coil 48 changes the energy generation (adapts the operating circuit) and reduces the energy harvesting to a second reduced level (since, for example, the external RF waves are not changed to the new resonant frequency). The change in harvested energy, reducing it by a significant amount such as by 90%, consequently turns off the heat treatment generated by the ferrite core 36. The modified level is at or at least at a threshold level that is sufficient to supply power to the microcontroller through the supporting connections to the rectifier and regulator. In this low power and treatment "off" mode, the heat treatment is controlled to allow the sensed temperature to drop to a threshold (or range) to activate the heat treatment. When the microcontroller 44 (from temperature information) determines this threshold is reached, microcontroller 44 signals semiconductor switch 46 to open and disable secondary coil 48.

Semiconductor switch 46 can also be used to transmit information to the external system using backscatter communications. Semiconductor switch 46 can be switched at a high frequency to modify the electromagnetic field of the electrical circuit to communicate digital information. An external system can use a sensor to monitor the characteristics of the electromagnetic field of the electrical circuit in operation. The quick changes can be detected by a sensor of the external system to detect information comprising an implant identifier and temperature sensed. The external system can demodulate the signal and detect the transmitted digital information. This can be performed using amplitude modulation.

This arrangement can provide that the implant is continuously operating during a treatment session by smoothly transitioning back and forth from a heat treatment mode to a standby mode (to allow the temperature level to drop to a desired level) to apply heat treatment up to a threshold level during the session. A session may for example take an hour to several hours.

The treatment can be applied during sessions held over an extended period such as once a day or week for several months in combination with other cancer treatment therapies such as those that do not rely on heat generation such as chemotherapy. The treatment can be performed at the same time or at different times. The combination can provide more effective results.

Microcontroller 44, rectifier, and regulator can be an integrated semiconductor circuit (individually or in combination).

Figure 4:
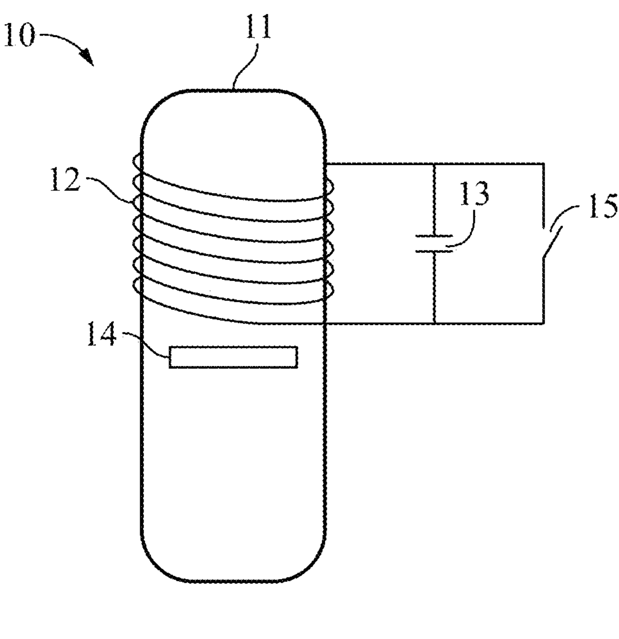
FIG. 4 is a diagram of an exemplary implant in accordance with one or more embodiments of the present invention(s).

FIG. 4 provides a diagram illustrating an example embodiment of the device 10 in accordance with another embodiment of the present invention. The switch 15 is connected in parallel to the capacitor 13. This can result in exposing the switch to high voltages. The switch should be of a semiconductor switch and should be a type that is a high voltage semiconductor switch that can prevent or protect against damage due to high voltages. Preferably, switch 15 includes, incorporates, or operates with circuitry such as a circuit component that configures the circuit to generate electricity at a second level capable of powering the operation of microcontroller 14 and able to "turn off" desired heating for treating cells. The microcontroller 14 controls when switch 15 and related circuitry are in a heat treatment mode (e.g., at a second power level) or "hold" mode when the microcontroller is operating using the transmitted RV waves converted into electricity and the heat treatment mode is "off") because the energy level is not sufficient to generate heat by the ferromagnetic core at a predetermined operational setting.

In the limited case that only a single implant is used, and it provides a real time temperature feedback to the controller 30, in some embodiments, the power of the external antenna 20 can be (constantly) adjusted (using information about the temperature of the heating portion of the implant) to maintain the desired temperature. This can for example be by having a real time temperature feedback to the controller 30. Especially if there is a single implant structure, the temperature would reflect the temperature of that single heating element. In this arrangement, the switch 15 and choke coil 16 can be removed. In one implementation, the operation would require constant or continuous updates (sufficient to maintain the desired temperature) and closed loop control with real-time communication (e.g., of temperature to allow for maintaining the temperature without variation that would affect performance).

Figure 5:
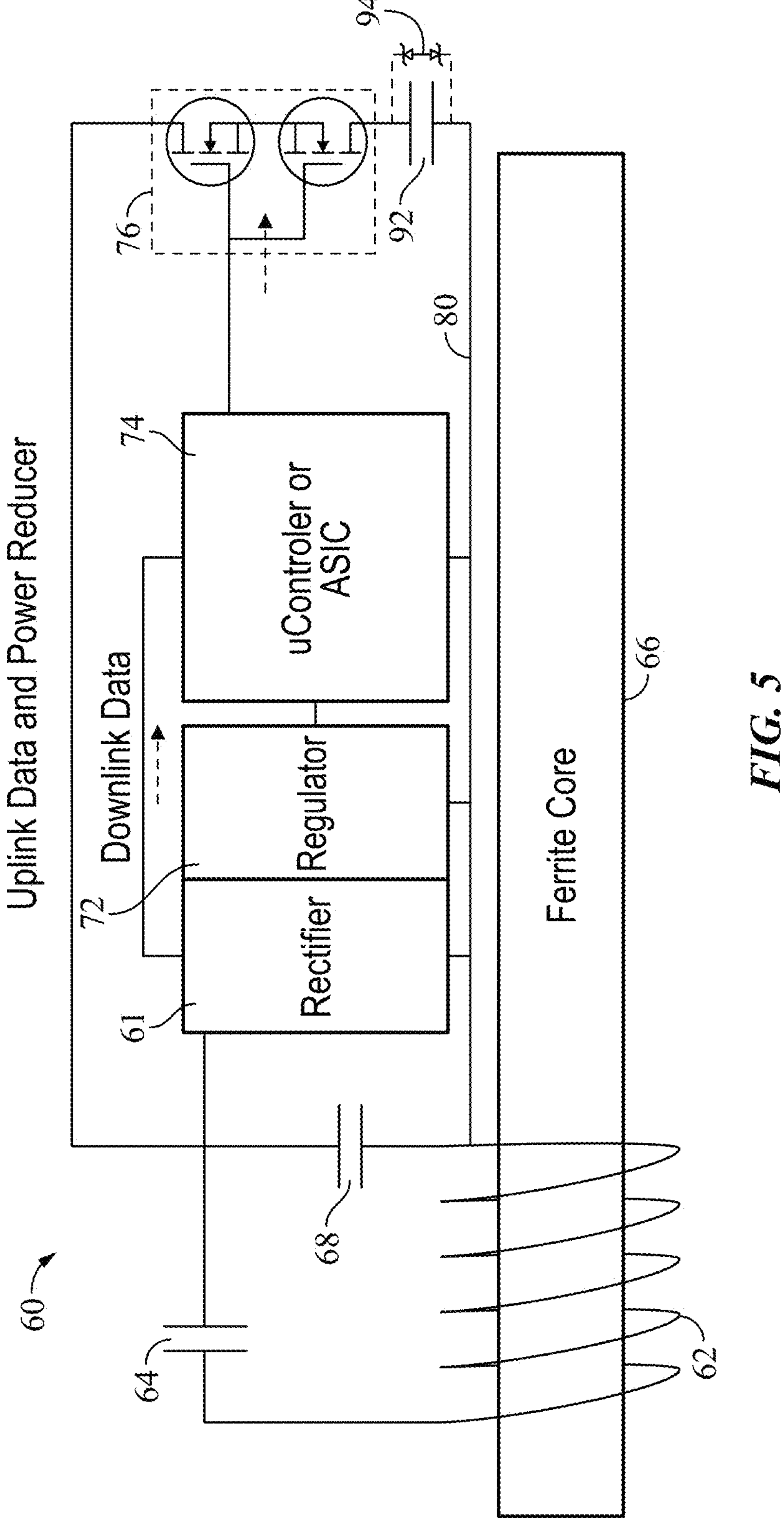
FIG. 5 is a circuit diagram of an exemplary implant, in accordance with one or more embodiments of the present invention(s).

With reference now to FIG. 5, electrical circuit 60 comprises coil 62, capacitor 64, ferrite core 66, capacitor 68, rectifier 61, regulator 72, microcontroller 74, and semiconductor switch 76. Electrical circuit 60 also includes capacitor 92 and/or Zener diodes 94 (back-to-back Zener diodes). Coil 62 in combination with capacitors 64 and 68 are selected to establish a desired resonant frequency for the electrical circuit 60. Equipment external to the body will be configured to transmit RF waves at that resonant frequency. Electric current generated by the arrangement is at a power level that causes the ferrite core 66 to generate heat at a desired/determined level (e.g., a temperature range of up to 20° C. above baseline, Watts of energy collected could be up to 5 W, a two hour treatment involving 36000 J) to treat tissue touching or adjacent to the implant (containing the electrical circuit 60). Capacitor 68 can also operate as a voltage divider. The current generated is tapped to flow current to the rectifier 61 (which rectifies the AC signal), which in turn supplies regulator 72 which conditions the electricity to provide a stable DC voltage power supply to the microcontroller 74. Circuitry in rectifier 61 or elsewhere can be configured to filter digital signals that were modulated into the transmitted RF waves. Amplitude modulation of the waves can be used to carry digital signals (e.g., transmitted by coil 20) to the electrical circuit 60. The circuitry can rectify and filter signals to generate "1"s and "0"s that were carried in the RF waves. The signals can carry information such as a temperature(s) to be stored in the microcontroller to use as the threshold or otherwise controlling when heating is turned "on" or "off."

Microcontroller 74 may include a temperature sensor or may receive temperature from another source such as a temperature sensor situated in electrical circuit 74 and physically external to microcontroller 74. The temperature sensor is used to determine the current temperature at or in close vicinity to the implant/electrical circuit. Depending on the configuration, equipment, and location and type of sensor, the microcontroller may have been previously configured to correlate or convert the sensed internal temperature to expected biological temperature external to the implant. Therefore, the sensed temperature may be representative of the current temperature and/or the heating temperature and based on predetermined calculations, it can be used to set the temperature setting for the electrical circuit.

Semiconductor switch 76 comprises, for example, two metal oxide semiconductor field effect transistors ("MOSFETs"). Microcontroller 74 is configured to have an output signal that turns both MOSFETs off or on.

When semiconductor switch 76 is closed, a path for current flow is established by the switch 76 through line 80. From a perspective of general circuit operation, when switch 76 is closed, a current path parallel to capacitor 68 is established and in effect, the current will, in general, flow through switch 76 and line 80. Switch 76 is positioned in a path that carries a current in a path parallel to the path of capacitor 68. This can include reducing or eliminating current flowing through capacitor 68. The activation or insertion of capacitor 92 when switch 76 is closed (both MOSFETs are turned on) modifies or modulates the resonant frequency configured by the inductors and capacitors in the circuit (62, 64, 68, and 92). The general formula for determining the resonant frequency for circuits based on the inductors and capacitors in the circuit can be used to calculate the change in the resonant frequency. The modification of the operation of the electrical circuit 60 when semiconductor switch 76 is activated may reduce the current flowing through coil 62. The modification shall disrupt the capability of electrical circuit 60 to generate energy by the inductance-capacitance arrangement when receiving the RF waves (which are transmitted at the resonant frequency of the electrical circuit 60 before the capacitor 92 is activated). Thus, the resonant frequency of the electrical circuit 60 changes, but the transmitted RF signal from the extern system does not change frequency. The misalignment or modulation transitions the electrical circuit 60 to generating power at lower level sufficient to power the microcontroller and would effectively turn off the heat treatment for the target area. This is an example of capacitive modulation or modification to disrupt the energy harvesting.

The change in harvested energy (between the two modes when switch 76 is activated or deactivated) reduces the generation by a significant amount such as by 90%, which consequently turns off the heat treatment generated by the ferrite core 66. The modified level is at or at least at a threshold level that is sufficient to supply power to the microcontroller through the supporting connections to the rectifier and regulator. In this low power/treatment "off" mode, the heat treatment is controlled to allow the sensed temperature to drop to a threshold (or range) to activate the heat treatment. When the microcontroller 74 (using temperature information) determines this threshold is reached, microcontroller 74 signals semiconductor switch 46 to open and disable the circuit path through line 80. This turns the heat treatment to commence again.

In some embodiments, back-to-back Zener diodes 94 can be part of the circuit. In FIG. 5, they are shown with a dashed line connection to indicate that the circuit 60 can be modified to replace capacitor 92 with back-to-back Zener diodes 94. To clarify, this is not to say that the arrangement cannot include embodiments that include both a capacitor 92 and back-to-back Zener diodes 94 (e.g., in series). The back-to-back Zener diodes 94 in operation ensure that the voltage is controlled such that it prevents a complete short circuit around capacitor 68 and microcontroller 74. With this avoidance, voltage sufficient to operate the microcontroller 74 can be established. This provides a load based modulation that inserts or activates back-to-back Zener diodes 94 that change the energy generation state of the electrical circuit 60.

Electrical circuit 60 operates in the same way as electrical circuit 35 of FIG. 3 in the operation of sending and receiving digital signals and related data, and with respect to the regulator rectifier 61, regulator 72 and microcontroller 74 arrangement.

Figure 6:
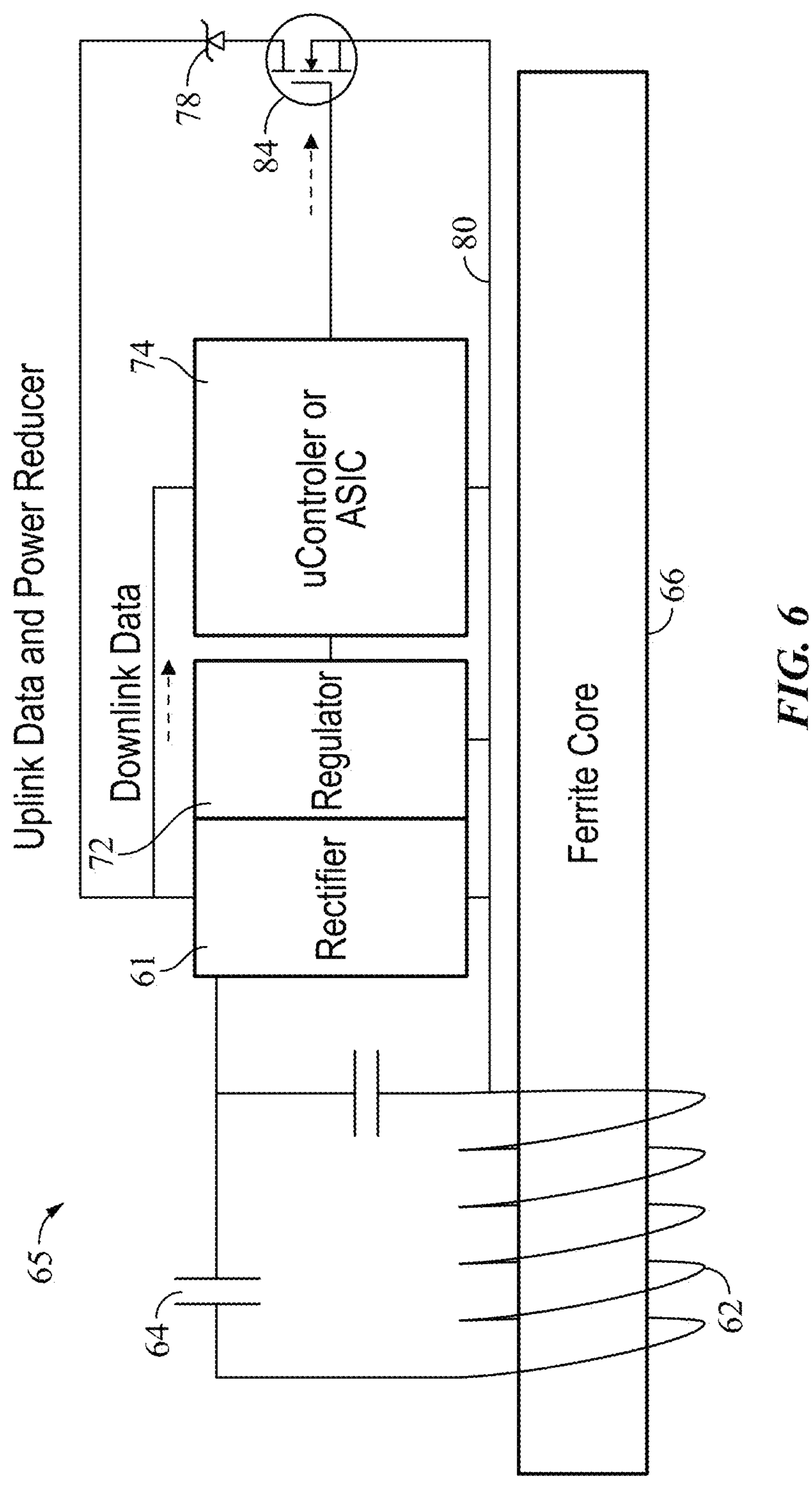
FIG. 6 is a circuit diagram of an exemplary implant, in accordance with one or more embodiments of the present invention(s).

With reference to FIG. 6, in some embodiments of electrical circuit 65 has a similar structure to electrical circuit 60 of FIG. 5 but with a variation involving a Zener diode. Electrical circuit 65 includes a Zener diode 78 and a semiconductor switch, a MOSFET 84. This arrangement operates similarly but would rectify the current flowing to Zener diode 78. Zener diode 78 can operate as a voltage regulator which can consequently affect the operation of current flowing in line 80 when switch 84 is closed. Zener diode 78 ensures that regulator 72 still has sufficient energy for operating microcontroller 74. This arrangement can disrupt the capability of the electrical circuit to capture energy from the transmitted RF waves by adding loading (when switched on). This is an example of load modulation or modification to disrupt the energy harvesting (e.g., inserting a load that disrupts the harvesting of energy by inserting the current path through the Zener diode 78).

This arrangement can provide that the implant is continuously operating during a treatment session by smoothly transitioning back and forth from a heat treatment mode to a standby mode (to allow the temperature level to drop to a desired level) to apply heat treatment up to a threshold level during the session. A session may for example take up to several hours.

The treatment can be applied during sessions held over an extended period such as once a day or week for several months in combination with other cancer treatment therapies such as those that do not rely on heat generation such as chemotherapy. The treatment can be performed at the same time or at different times. The combination can provide more effective results.

As would be understood, FIGS. 5 and 6 are not prepared to be the actual physical size or positioning of the device.

Example operational data for the device of FIG. 1-6 is an external electrical drive power at 10 W, 10 Vpeak for implants 3 cm deep (meaning depth inside the body) and scaled approximately as depth squared. Therefore, 9 cm deep would be 90 W. For reference this is on par with an incandescent lightbulb. A personal heating pad is 250 W so even at 100 W this could easily be integrated into a therapy system. In operation, heat treatment can be tightly controlled by the microcontroller such as signaling the switch to turn on heating for less than 1 second to provide heat treatment and then perform cooling as the power dissipates.

The external system such as computer 30 and coil 20 can be configured with circuitry to receive and transmit energy waves (the RF waves) and to receive and transmit digital signals using an inductance/capacitance arrangement.

The microcontroller can be a semiconductor integrated circuit such as an application specific integrated circuit (ASIC), Field Programmable Gate Arrays (FPGAs), or an integrated circuit that is configured to operate as described herein. The microcontroller may include a temperature sensor as part of the integrated circuit or could be connected with a port or line to receive signals representative of the current temperature of the tissue being treated. The microcontroller can include memory to support the operation of the implant and microcontroller. The memory, rectifier, regulator, switch, or other components can be fixed on the same support. In some embodiments some or all function blocks including memory, rectifier, regulator and switch may be integrated with the microcontroller. In certain embodiments the microcontroller, rectifier, regulator and switch may be a single component (ASIC) or may be constructed from two or more discrete elements. Given that the electrical circuit is a mix of analog and digital electronic components, some components such as a Zener diode, primary coil, or ferromagnetic core are not typically made using integrated circuit semiconductor fabrication processing and therefore would be physically separate from the integrated circuit components such as the microcontroller. The rectifier and regulator are typically implemented using semiconductor integrated circuits. The memory may comprise non-transitory media (memory) that stored instructions to execute the described process using the microcontroller. If desired, the microcontroller can be configured to be hardwired using programmable elements without relying on using instructions from a memory. In some instances, some functions of the microcontroller may be implemented on a secondary microchip. For example, memory and data may be stored in a secondary chip to the microcontroller In the illustrated exemplary embodiments, the electrical circuit comprises one or more components that selectively disrupt or reduce wireless energy generation. Such a function is performed by the illustrated circuit components in interaction with other circuit components such as in FIG. 3, switch 46 and coil 48 working under the control of microcontroller 44 to disrupt the operation of coil 32.

Figure 7:
FIG. 7 is a diagram of a relative size of individual implants as illustrative embodiments of the present invention(s).

FIG. 7 provides context for illustrating an expected size for some embodiments of the implant. Two implants are shown relative to a U.S. one cent coin. The size dimensions are 1.5 mm in diameter×14 mm in length and in general can range from 5 mm to 20 mm in length and 1 mm to 3 mm in diameter. Preferably, the enclosure, casing, or housing of the implant is adapted to seal the electronics inside to prevent liquid from reaching the electronics or liquid sensitive components. The materials would be of the type that allows for the RF waves to reach the electrical circuit without blocking or substantially interfering (e.g., it is not made of a metal that can interfere with the waves) such as glass or alumina. Epoxy, for example, or other materials can be used to seal the structure. The structure can be cylindrical as shown because it is particularly suited for injection into the body, but other arrangements are contemplated. The material is preferably the type that does not negatively interact to the human body when embedded in the body. In some instances, features may be added to the outside of the device to prevent migration in the body and facilitate removal.

It should be understood that the illustrated embodiments are not necessarily mutually exclusive. In other words, inductive, capacitive, and load modulation are not necessarily distinct solutions but can be combined.

Inductive, capacitive, or load modulation is being used to refer to the primary change is that particular modulation. It does not necessarily mean that no other modulation will occur.

Figure 8:
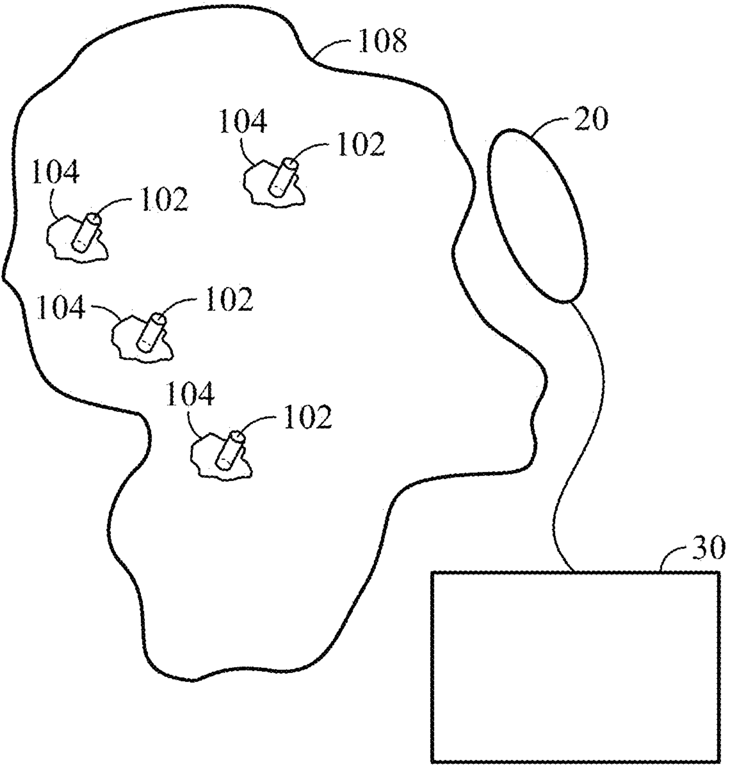
FIG. 8 is a system diagram illustrative of a system using multiple implants in accordance with one or more embodiments of the present invention(s).

FIG. 8 illustrates that multiple implants 102 can be positioned in a body region 108 to provide treatment using the heat treatment capability of the implants. The implants 102 are positioned in spaced-apart locations and in a location in which the implant 102 is in a physical location in relation to tissue that that is the target of the treatment 104 to apply heat treatment to target 104. For example, an implant 102 can be inserted to be in direct physical contact with the cancerous cells or other target for treatment. The position can be such that the implant 102 is close enough to apply the desired level of heat which may not necessarily always require direct physical contact. Each implant 102 can be configured to have its own identifier and to transmit the identifier (and sensed temperature) to the external system comprising computer 30. In this arrangement, a coil 20 can transmit RF waves to provide energy to the implants 102 at a frequency, which is also the turned resonant frequency of each implant 102. Computer 30 can receive identifiers and temperature information to confirm that treatment is performed. Each implant, for example, based on the distance to coil 20, may operate slightly differently. Since implant 102 has internal control of whether to activate or deactivate the heat treatment based on sensed temperature by each corresponding implant 102, implant 102 can independently activate and deactivate to apply the predetermined level of heat based on that implant's 102 local conditions with respect to temperature, power, tissue, etc.

With respect to "on" or "off" states of semiconductor switches, such devices may have a negligible of leakage current in an "off" state. This is generally understood when discussing "on/off" or "activate/deactivated" states of semiconductor switches.

With respect to generating heat, in general, electrical circuit components inherently generate heat from the operation of the component. It would be understood that the contribution of heat from such elements in the electrical circuit are minimal and the heat treatment when active is almost entirely (e.g., more than 80%) from the ferromagnetic core.

When discussing the resonant frequency, it is understood that the transmitted RF wave frequency does not necessarily have to be precisely at the resonant frequency, meaning that the term can include +/−10% of the resonant frequency.

Applications of the system, treatment, or device as presently contemplated is primarily in the field of oncology (to treat cells) but may also include neurological applications including quieting nerves associated with pain pathways, hypertension and inflammation. In these applications, the configuration will have a maximum setpoint temperature to avoid nerve damage.

In the oncology setting, the system allows controlled thermal doses to be applied when/where they have the highest utility, such as daily or weekly heating, to ablate tumor growth near a critical structure or when paired with chemo- or immunological therapy infusions where short-term heating could weaken the tumor tissue or make them more amenable to these therapies.

In this scenario, the injectable device is placed in the tumor by a surgeon using an image guided system such as fluoroscopy or ultrasound. Following implantation, the patient undergoes a standard series of chemotherapy sessions which involve visiting a chemo-infusion center where specific doses are applied in an out-patient setting. Before or during chemotherapy infusion an external coil 20 could be used to heat the implantable device, and the surrounding tumor, by wireless, providing power with an external device. The heat increases the effectiveness and efficacy of the chemotherapy by weakening or preconditioning the diseased cells which are more sensitive to heat than healthy cells. Using heating pads or other non-specific heating devices would also increase the interaction of the chemotherapy with healthy tissue.

Treatment can also include using the heat as a 'signal' to activate temperature sensitive chemicals reactions and cells.

Treatments can be for humans but are not necessarily limited to humans and can include mammals.

Although embodiments of the present invention are particularly suitable for weakening or preconditioning diseased cells, the device can also be used to ablate diseased cells.

One or more coils 20 can be installed in a chair and positioned in or more locations. The chair can be used for a patient receiving other forms of treatment such as chemotherapy. The coil(s) can be connected to the externa system and can generate the discussed RF energy waves to transmit energy to the implants described herein that are embedded in the body of a patient for treatment. This arrangement can provide the ability to provide the treatment simultaneously or approximately at the same time. In some instances, a non-resonant antenna external to the body may be used to measure the backscattered energy from the implant.

It should be understood that variations, clarifications, or modifications are contemplated. Applications of the technology to other fields are also contemplated.

The external system may comprise a computer that includes a processor and a main memory, such as a random access memory (RAM) or other dynamic storage device, coupled to bus for storing information and instructions to be executed by a processor. Main memory also may be used for storing temporary variables or other intermediate information during execution of instructions to be executed by the processor. Such instructions, when stored in non-transitory storage media accessible to the processor, render the computer into a special-purpose machine that is customized to perform the operations specified in the instructions.

The computer further includes a read only memory (ROM) or other static storage device coupled to a bus for storing static information and instructions for the processor. A storage device, such as a magnetic disk or optical disk, is provided and coupled to bus for storing information and instructions.

The computer may be coupled via bus to a display, such as a cathode ray tube (CRT), for displaying information to a computer user. An input device, including alphanumeric and other keys, is coupled to bus for communicating information and command selections to processor. Another type of user input device is cursor control, such as a mouse, a trackball, or cursor direction keys for communicating direction information and command selections to processor and for controlling cursor movement on display. This input device typically has two degrees of freedom in two axes, a first axis (e.g., x) and a second axis (e.g., y), that allows the device to specify positions in a plane.

The computer may implement the techniques described herein using customized hard-wired logic, one or more ASICs or FPGAs, firmware and/or program logic which in combination with the computer system causes or programs the computer to be a special-purpose machine. A computer can perform operations in response to the processor executing one or more sequences of one or more instructions contained in main memory. Such instructions may be read into main memory from another storage medium, such as storage device. Execution of the sequences of instructions contained in main memory causes the processor to perform the process steps described herein. In alternative embodiments, hard-wired circuitry may be used in place of or in combination with software instructions.

The term storage media as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device. Volatile media includes dynamic memory, such as main memory. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprises a bus. Transmission media can also take the form of acoustic or light waves, such as those generated during radio-wave and infra-red data communications.

Exemplary systems, devices, and methods are described for illustrative purposes. Further, since numerous modifications and changes will readily be apparent to those having ordinary skill in the art, it is not desired to necessarily limit the invention to the exact constructions as demonstrated in this disclosure. Accordingly, all suitable modifications and equivalents may be resorted to falling within the scope of the invention.

It should be understood that claims that include fewer limitations, broader claims, such as claims without requiring a certain feature or process step in the appended claim or in the specification, clarifications to the claim elements, different combinations, and alternative implementations based on the specification, or different uses, are also contemplated by the embodiments of the present invention.

It should be understood that combinations of described features or steps are contemplated even if they are not described directly together or not in the same context.

It should be understood that combinations of described features or steps are contemplated even if they are not described directly together or not in the same context.

The passive voice such as using the words "may" and "can" is sometimes used as a precaution in the present description to explicitly indicate that this is one embodiment, but the description should not be understood to be the only embodiment. To clarify, the lack of such use of terminology similarly provides exemplary statements. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

As used herein, the term "about" refers to a range that is +10% from the values recited within the context specifically used. Also, if "about" is not specified in association with a number or range, it should be understood that it is contemplated. Every point in a range is also considered as having particular relevance without having to be explicitly expressed herein.

The terms or words that are used herein are directed to those of ordinary skill in the art in this field of technology and the meaning of those terms or words will be understood from terminology used in that field or can be reasonably interpreted based on the plain English meaning of the words in conjunction with knowledge in this field of technology. This includes an understanding of implicit features that for example may involve multiple possibilities, but to a person of ordinary skill in the art a reasonable or primary understanding or meaning is understood.

What is claimed is:

1. A medical treatment implant for treating cancer for an extended period in a patient's body, comprising:

an electrical circuit comprising a microcontroller that is configured to store a threshold temperature;

a first inductor;

a first capacitor, a temperature sensor, a ferromagnetic core that is adapted to interact with the inductor to generate heat to treat a target area of a body, wherein the first inductor and first capacitor configure a resonant frequency of the electrical circuit, and are adapted to receive wireless electromagnetic waves and in response, produce power at a first level that is capable of powering operation of the microcontroller and the ferromagnetic core to treat a target area of the body; and a semiconductor switch that is adapted to reduce power to a second level below the first level based on the temperature sensor sensing the threshold temperature, by selectively activating a second inductor, a second capacitor, or an additional circuit component, wherein the second level is capable of powering operation of the microcontroller and turns off the heating.

2. The medical treatment implant of claim 1 wherein the electrical circuit comprising the second inductor adapted to be associated with the ferromagnetic core and when activated, produces a magnetic field that modifies a magnetic field associated with the first inductor.

3. The medical implant of claim 2 wherein the semiconductor switch comprises one or more metal oxide semiconductor field effect transistors (MOSFETs).

4. The medical implant of claim 1 wherein the electrical circuit includes a rectifier and a regulator that are adapted to produce a DC voltage that powers the microcontroller.

5. The medical implant of claim 1 wherein the electrical circuit, using the first inductor and first capacitor, is configured to receive amplitude modulated RF waves that carry digital information.

6. The medical implant of claim 1 wherein the electrical circuit is adapted to transmit information using backscatter communications.

7. The medical implant of claim 1 wherein the electrical circuit is adapted to selectively vary power consumption among two or more levels that communicates digital information to an external device that is monitoring the medical implant.

8. The medical implant of claim 1 wherein the electrical circuit is configured to store an identifier and vary power use of the electrical circuit to communicate the identifier to an external device.

9. The medical implant of claim 1 wherein the semiconductor switch selectively inserts loading that steers a portion of a current through a Zener diode.

10. The medical implant of claim 1 wherein the electrical circuit is configured to automatically and independently active or deactivate the semiconductor switch based on temperature.

11. The medical implant of claim 1 wherein the microcontroller comprises a temperature sensor.

12. The medical implant of claim 1 wherein a temperature sensor is included that is configured to communicate with the microcontroller.

13. The medical implant of claim 1 wherein the electrical circuit is configured to transmit a local temperature.

14. A system comprising, a plurality of heat generating wireless implants, wherein each implant comprises a ferromagnetic core that generates heat to treat adjacent cancer cells in a body, a semiconductor switch that automatically and independently activates the ferromagnetic core based on temperature sensed at or about the implant to operate the implant to stay within a sensed temperature range of 37° C. to 60° C., and an inductor and capacitor combination that converts RF waves to energy that operates the implant, and a microcontroller that varies current load in the implant to wireless transmit an implant identifier and sensed temperature; and a device positioned external to the body that generates RF waves to provide wireless power to the implants and receives identifiers and sensed temperatures from individual implants.

15. The system of claim 14 wherein the device is configured to transmit an RF wave at a certain frequency whereby the implants are configured to generate heat selectively at different locations based on the implant's sensed temperature.

16. The system of claim 14 wherein each implant is configured to transmit the identifier using backscatter communications.

17. The system of claim 14 wherein each implant is configured to operate to stay within a sensed temperature of 38° C. to 43° C.

18. The system of claim 14 wherein the semiconductor switch modifies inductance, capacitance, or loading characteristic of an electrical circuit operating in the implant to activate or deactivate heating by the ferromagnetic core that treats a targeted area of the body.

19. The system of claim 14 wherein the semiconductor switch is a single MOSFET.

20. The system of claim 14 wherein the implant receives and stores a maximum temperature transmitted from the external device.

21. The system of claim 20 wherein the implant limits heating once the measured temperature surpasses the stored maximum temperature.

* * * * *